United States Patent [19]
Dreher

[11] Patent Number: 6,112,114
[45] Date of Patent: Aug. 29, 2000

[54] EYE EXAMINATION APPARATUS EMPLOYING POLARIZED LIGHT PROBE

[75] Inventor: Andreas W. Dreher, Escondido, Calif.

[73] Assignee: Laser Diagnostic Technologies, Inc., San Diego, Calif.

[21] Appl. No.: 09/090,436

[22] Filed: Jun. 4, 1998

Related U.S. Application Data

[63] Continuation-in-part of application No. 08/229,151, Apr. 18, 1994, Pat. No. 5,787,890, which is a continuation-in-part of application No. 07/808,479, Dec. 16, 1991, Pat. No. 5,303, 709.

[51] Int. Cl.[7] ........................................... A61B 3/10
[52] U.S. Cl. .................. 600/476; 600/558; 351/215; 351/221
[58] Field of Search .................................. 600/318, 319, 600/320, 321, 476, 473, 558; 351/205, 206, 221, 215

[56] References Cited

U.S. PATENT DOCUMENTS

| | | |
|---|---|---|
| 3,963,019 | 6/1976 | Quandt ..................................... 600/319 |
| 4,711,540 | 12/1987 | Yoshino . |
| 4,838,683 | 6/1989 | Ichihashi et al. ........................ 351/221 |
| 4,883,061 | 11/1989 | Zeimer . |
| 5,152,295 | 10/1992 | Kobayashi et al. . |
| 5,177,511 | 1/1993 | Feuerstein et al. ....................... 351/205 |
| 5,209,231 | 5/1993 | Cote et al. ............................... 600/319 |
| 5,609,159 | 3/1997 | Kandel et al. ........................... 600/558 |
| 5,787,890 | 8/1998 | Reiter et al. ............................ 600/476 |
| 5,894,338 | 4/1999 | Miehle et al. ........................... 351/206 |

Primary Examiner—Ruth S. Smith
Attorney, Agent, or Firm—John L. Rogitz

[57] ABSTRACT

Apparatus is provided for determining the topography, thickness, and fiber orientation of the nerve fiber layer at the fundus of the eye by measuring the polarization shift induced in a return beam of polarized light which is reflected at the ocular fundus from an incident beam of a known polarization state. A corneal polarization compensator effectively cancels the birefringent effects of the cornea and other portions of the eye anterior to the fundus, so that clinically meaningful results are produced. A method for directing a measurement beam into the eye is also disclosed.

12 Claims, 9 Drawing Sheets

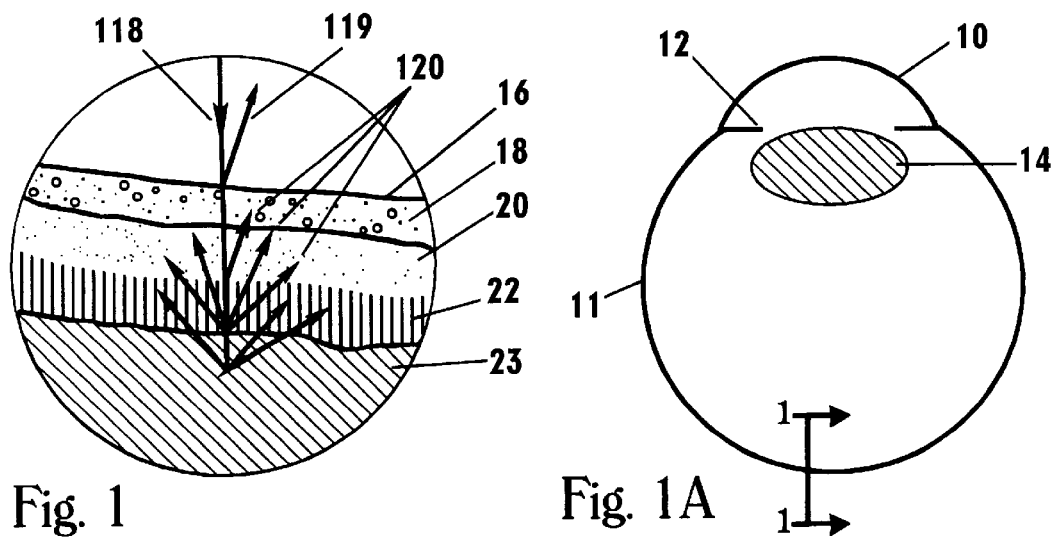
Fig. 1
Fig. 1A
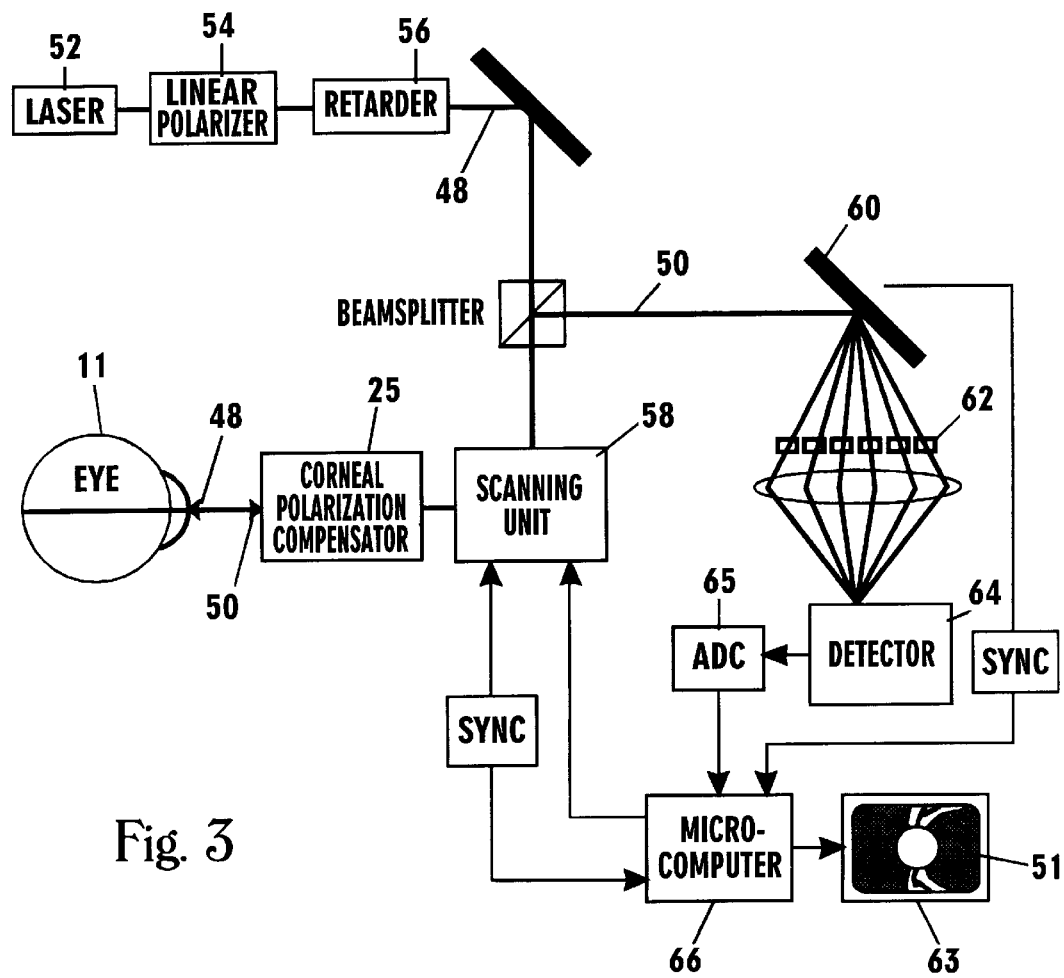
Fig. 3

Fig. 10
Fig. 11
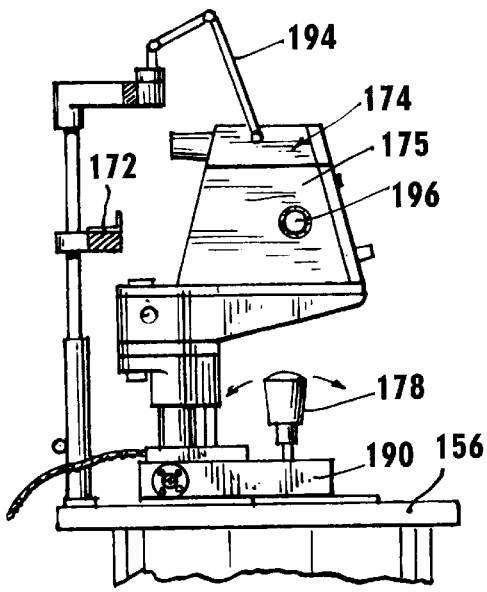
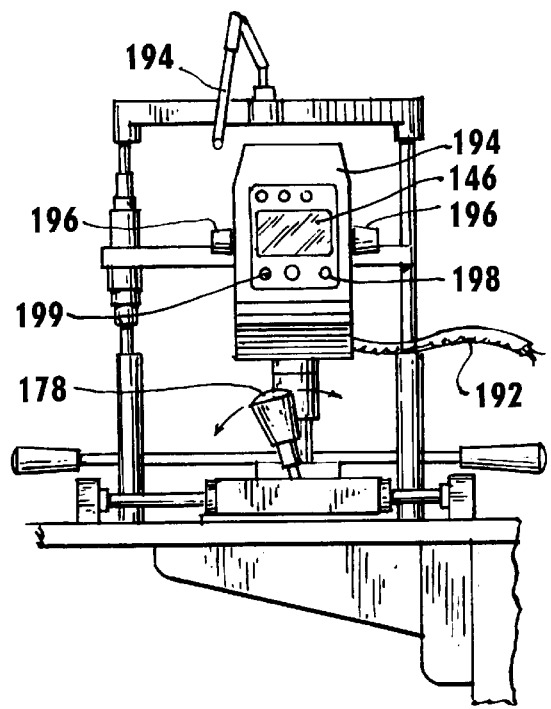
Fig. 12
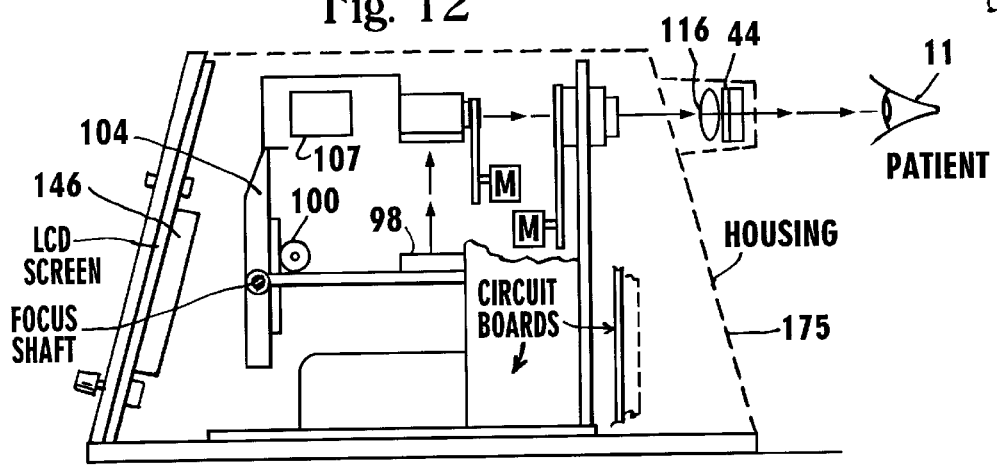
Fig. 13
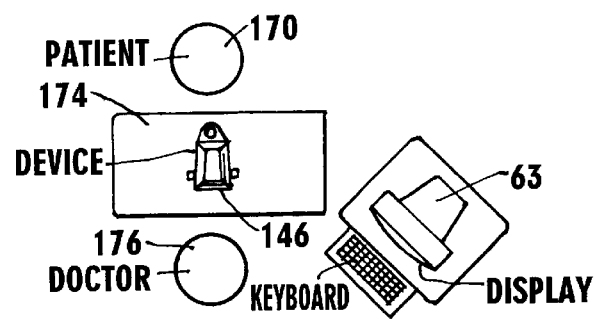

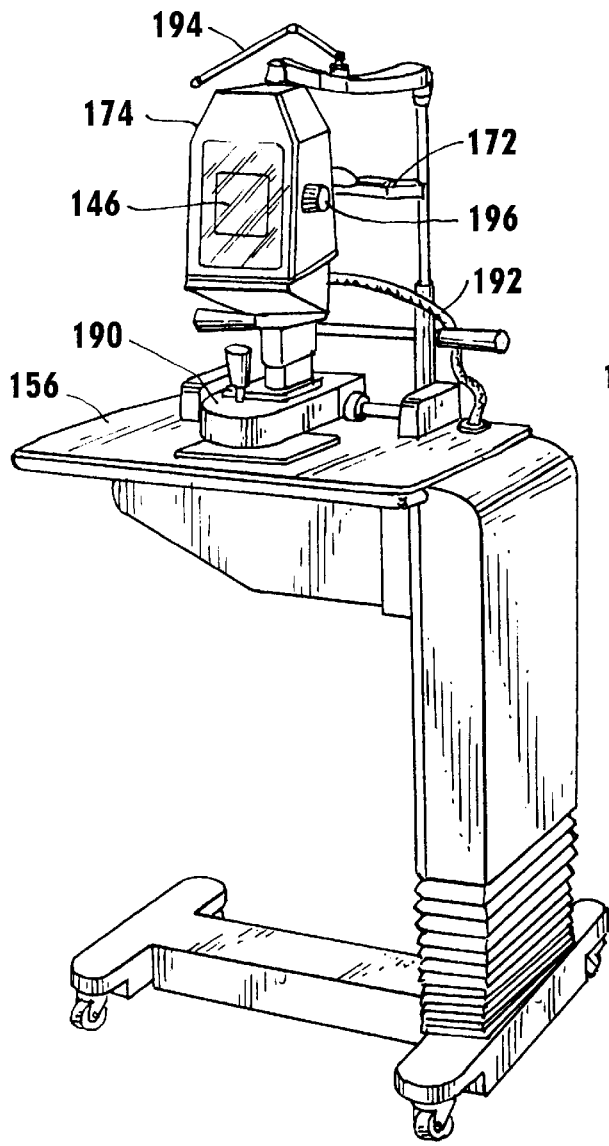
Fig. 15
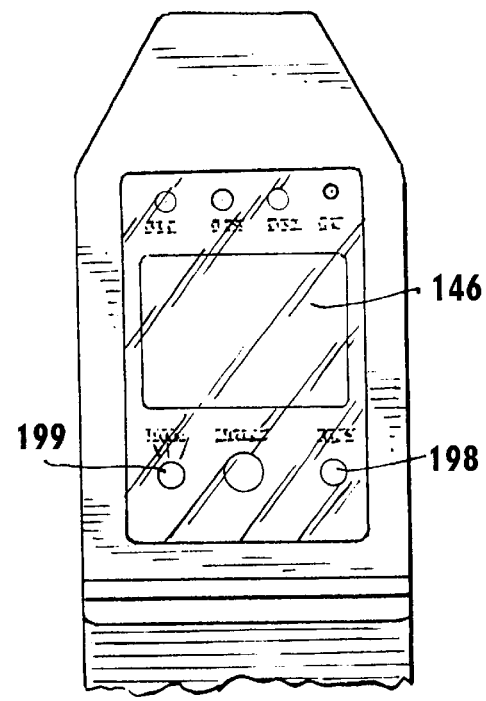
Fig. 16
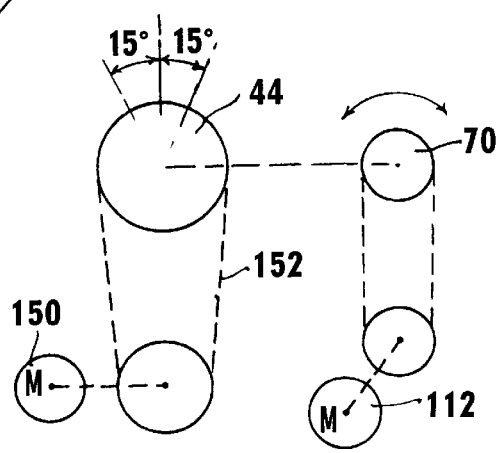
Fig. 14
Fig. 17

EYE EXAMINATION APPARATUS EMPLOYING POLARIZED LIGHT PROBE

RELATED APPLICATIONS

This application is a CIP application that claims priority from allowed U.S. patent application Ser. No. 08/229,151, filed Apr. 18, 1994, now U.S. Pat. No. 5,787,890 which in turn is a CIP of U.S. patent application Ser. No. 07/808,479, filed Dec. 16, 1991, now U.S. Pat. No. 5,303,709, priority to both of which is hereby claimed.

FIELD OF THE INVENTION

The present invention relates to an apparatus for assessing the thickness, topography and nerve fiber orientation of the retinal nerve fiber layer by measuring the polarization effect of the nerve fiber layer on an impinging light beam while eliminating the obscuring polarizing effects of the anterior segment of the eye.

BACKGROUND

The retinal nerve fiber layer is the innermost layer of the retina, and consists of the nerve fibers (ganglion cell axons) which transmit the visual signal from the photoreceptors to the brain. With the onset of glaucoma and other optic neuropathies, there is increasing damage to the nerve fibers, causing impaired vision or blindness. Glaucoma and other diseases must be diagnosed early on to slow or stop this process, and for an accurate diagnosis it is important to ascertain the presence and extent of any such damage.

Because the nerve fiber layer is very thin (about 30 $\mu$m to 150 $\mu$m) and the optical depth resolution of the human eye is only about 200 $\mu$m to 300 $\mu$m, measurement methods based on optical imaging are not sufficient to accurately measure the thickness of the nerve fiber layer. In addition, the retinal nerve fiber layer is transparent, which makes it even more difficult to assess it by imaging means.

Conventionally, assessment of damage in the nerve fiber layer is made with red-free fundus photography. Visible light of shorter wavelength ("red-free") is employed to achieve increased scattering of light within the nerve fiber layer, improving the visibility of the otherwise transparent layer. However, no quantitative measurements of the nerve fiber properties can be obtained with this method.

Other, more indirect methods have been developed to estimate nerve fiber layer thickness. Zeimer (U.S. Pat. No. 4,883,061) described a geometric method that uses the projection of a line onto the fundus. The reflections of the line from the anterior and posterior surfaces of the retina are used to measure the thickness of the total retina which is about 500 $\mu$m to 700 $\mu$m thick. The resolution of this method is, however, not sufficient to measure the thickness of the nerve fiber layer which is only one thin layer of many layers of the retina, making up possibly one-tenth of the total retinal thickness. Even with as little margin for error as ±5%, the measurement error could be as great as the measurement itself.

Another indirect approach to assessing the nerve fiber layer condition is to measure the topography of the internal limiting membrane which forms the anterior surface of the nerve fiber layer. The result of this type of measurement, however, is the measurement of only one surface of the nerve fiber layer. Absolute thickness measurement of the nerve fiber layer is not possible. Topography instruments (i.e. U.S. Pat. No. 4,900,144) employ means of detecting intensity of light reflected from the fundus surface (internal limiting membrane). The systems determine the focus position of maximum light reflection and assume this focus position to be the position of the internal limiting membrane. In reality, however, the light detected by these systems is composed of light deriving from many different retinal layers, and the position of the maximum light reflection is usually displaced rearwardly of the membrane an indeterminate amount, producing false readings.

Geometric techniques alone will not produce clinically meaningful measurements of nerve fiber layer thickness or topography as proven by the results obtained from these techniques. The characteristics of the eye must be probed beyond its geometry, which the instant inventors have done. The result is a measuring apparatus which takes advantage of differences in polarization properties of various layers of the eye to augment or replace geometry-based techniques for relative spatial measurements in vivo, and on the eye.

The present invention further recognizes that the on site collection of data from a patient need not be conducted by a doctor and indeed need not be analyzed on site at all. Instead, as recognized herein it might be desired for convenience and cost purposes that a technician collect the data from a patient, and that the data be sent off-site for analysis.

SUMMARY OF THE INVENTION

The nerve fiber layer consists of parallel microfibers with diameters smaller than the wavelength of visible light. Such a medium shows form-birefringence with an optic axis parallel to the direction of the fibers. Polarized light passing through the form-birefringent nerve fiber layer experiences a change in its state of polarization that is linearly correlated with the thickness of the nerve fiber layer and substantially independent of any other layers of the retina. By measuring the change in the state of polarization of light double-passing through the nerve fiber layer, the polarization properties of the nerve fiber layer can be assessed, and the thickness therefore determined, independent from any dimension characteristics of the other retinal layers which lack birefringence.

Although this technique effectively isolates nerve fiber layer measurements from influences of other retinal layers, in order to perform in-vivo measurements of the nerve fiber layer, the measuring light has to penetrate the cornea and the lens of the human eye (the anterior segment). Unlike most of the retina, these elements also have polarization properties that would change the state of polarization of light. In order to measure the isolated polarization properties of the retinal nerve fiber layer in vivo, the polarization effects of the cornea and lens have to be compensated or the results would be meaningless.

The principle object of this invention is to objectively measure the thickness of the retinal nerve fiber layer by measuring the spatially resolved polarization properties of the fundus after compensating for the polarization effects of the anterior segment of the eye. This method allows, for the first time, to exclusively measure the absolute thickness of the retinal nerve fiber layer, providing the ophthalmologist a tool to help diagnose eye diseases earlier than currently possible.

In another aspect, a computer program device is disclosed which includes a computer program storage device readable by a digital processing apparatus, and a program means on the program storage device. The program includes instructions that are executable by the digital processing apparatus for performing method steps for directing a diagnostic beam onto an eye of a patient.

In accordance with the present invention, the method steps include receiving an image signal representative of a fundus of the eye. In response to the image signal, one or more images of the eye is generated, with at least one of the images being centered on the optic nerve location in the fundus in response to the image signal.

Preferably, the image signal has an intensity, and the method steps include generating at least one control signal in response to the image signal. At least one of the control signals is a focus signal for causing a focussing lens to move such that the intensity of the image signal is maximized. A computer is also disclosed that accesses a normative database to compare the image signal to at least some elements in the database and to generate an analysis signal in response thereto.

In another aspect, a method is disclosed for diagnosing maladies of an eye. The method includes directing at least one guide beam toward a pupil of the eye, and transmitting at least one diagnostic beam along the guide beam. Further, the method includes receiving at least one reflection of the diagnostic beam, and transforming the reflection into an image signal. Based on the image signal, the diagnostic beam is focussed onto an optic nerve location in the eye.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a diagrammatic section taken through line 1—1 of FIG. 1a;

FIG. 1a is a diagrammatic view of the eye identifying parts of the anterior segment;

FIG. 3 illustrates diagrammatically one manner in which the nerve fiber layer thickness is mapped with the use of a sequential array of polarizers of different states of polarization;

FIG. 10 is a side elevation view of the apparatus;

FIG. 11 is a front elevation view of the apparatus, seen from the orientation of the operator;

FIG. 12 is a diagrammatic side elevation view illustrating the relative positioning of the patient and the apparatus;

FIG. 13 is a top diagrammatic planned view of the layout of the equipment illustrating the relative positions of the apparatus, the doctor and the patient;

FIG. 14 is a simple diagrammatic representation of the eye of the patient as seen from the front, with the annular light ring centered on the pupil;

FIG. 15 is a prospective view of the apparatus illustrated in its entirety as implemented on a mobile base;

FIG. 16 is a fragmentary detail of the front panel of the apparatus shown in elevation;

FIG. 17 is a diagrammatic representation of the left/right eye switching mechanism of the anterior segment polarization compensator and of the polarization rotator;

DETAILED DESCRIPTION OF THE PREFERRED EMBODIMENT

Figure 2:
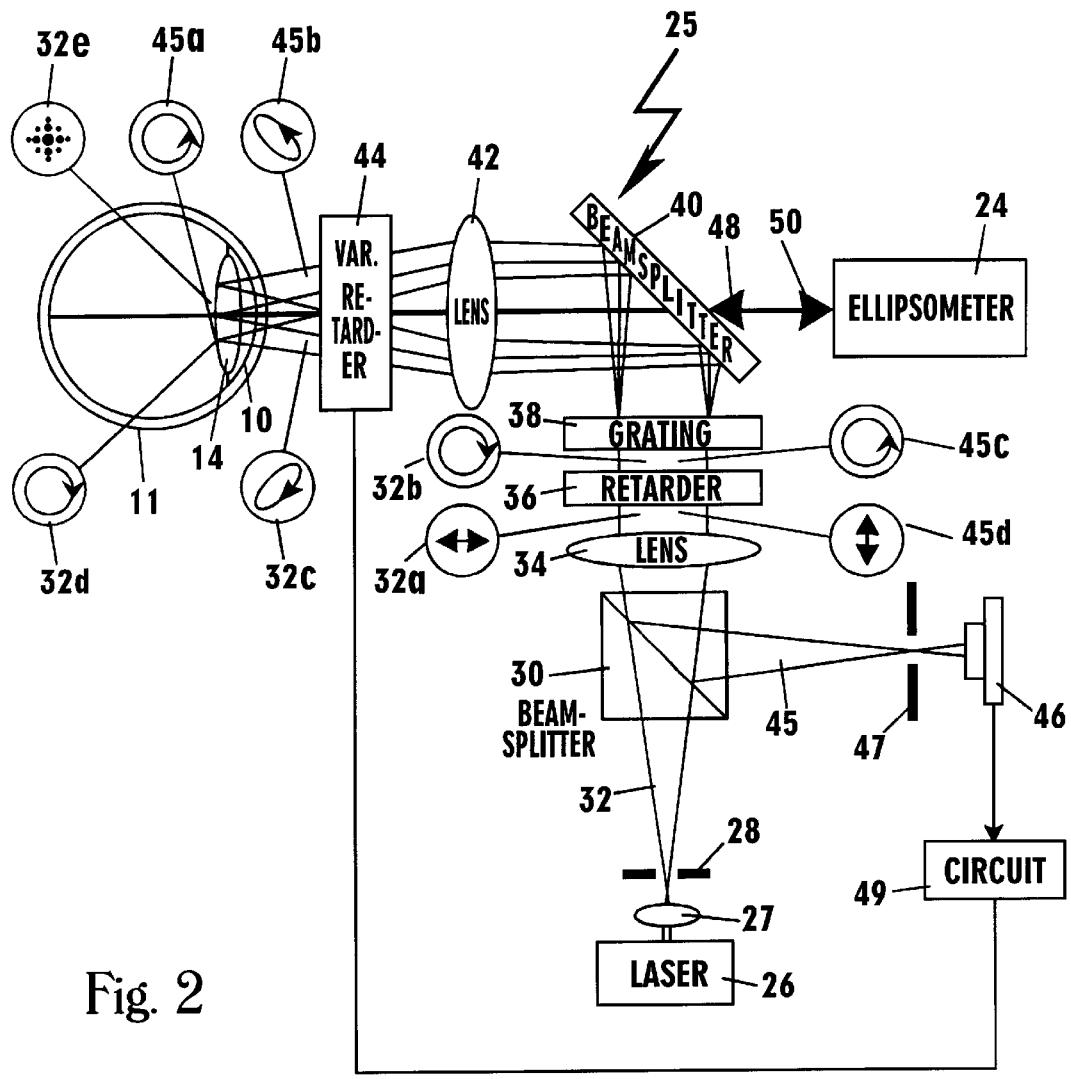
FIG. 2 illustrates diagrammatically the main parts of a principle embodiment of the corneal polarization compensator using an ellipsometer.

FIGS. 1 and 1A illustrate the eye 11, in which the cornea 10 senses as the foremost, transparent portion of the eye, behind which is the iris 12 and the lens 14. The interior of the eye 11 is filled with vitreous and at the back of the eye is the retina, composed of the layers illustrated in FIG. 1, including the internal limiting membrane 16, the nerve fiber layer 18, the receptor system 20, the retinal pigment epithelium 22, and the choroid 23. All eye structure forward of the membrane 16 is considered the anterior segment of the eye for purposes of this disclosure and claim definitions.

The invention concerns itself primarily with the cornea, the lens, and the nerve fiber layer 18. It is this nerve fiber layer's topographic and thickness measurements which are crucial to the diagnosis of certain diseases, among them being glaucoma. The orientation of the fibers is also useful to a general understanding of a particular eye, and in interpreting the thickness and tomograph data. Since fiber orientation has heretofore been unascertainable, it is expected that with time this information will be relied upon as a diagnostic indicator.

As indicated above, the nerve fiber layer 18 has birefringent properties. A polarized light ray incident on the surface of a birefringent medium, with its optic axis parallel to the surface of the medium, will split into two rays of different polarization states, propagating in the same direction but with different velocities. The difference in travelling velocity causes a shift in phase between the two exiting rays. This is called "retardation", and results in altering the polarization of the light. The thicker the birefringent medium, the greater is the retardation of transmitted light. A so called "quarter wave" retarder incorporates a birefringent medium that retards the phase of one of the rays 90 degrees relative to the other, converting linear polarization to circular polarization, and vice-versa.

In addition to the nerve fiber layer 18, the cornea and the lens also have birefringent properties, although the birefringence of the lens is small compared to the cornea. There are no other known birefringent layers in the eye.

Turning now to FIG. 2, a complete system for diagnosing the thickness of the nerve fiber layer is diagrammatically shown. All of the structure in FIG. 2 except for the ellipsometer 24 is for the purpose of compensating for the polarization shifting caused by the cornea and lens. (In this disclosure and claims, polarization "shifting" or "alteration" refer to all types of polarization changes, including rotation of the polarization axis of polarized light, the change of linear to elliptical or circularly polarized light or vice-versa, change in the polarization level, and any combination of these). The term "corneal polarization compensator" is used for describing the device for compensating for the polarization effect of the anterior segment of the eye.

The ellipsometer 24 is an instrument which accurately identifies the polarization state of a light beam. In this application, it makes possible the assessment or the nature and degree of polarization state shifting of light which double-passes the nerve fiber layer. This shift correlates to the thickness of the nerve fiber layer once the corneal polarization compensation has been effected. The thinner this layer is, the more advanced is the eye disease, as a general rule.

The corneal polarization compensator 25 utilizes a laser diode 26 which provides a beam of light that is focused by a lens 27 onto the pinhole 28 and expands as a cone until it impinges upon the polarizing beamsplitter 30. This beamsplitter has two purposes, the first of which is to polarize the incident compensation beam 32, which it does as is indicated by the legend indicated at 32a, illustrating the linear transverse polarization that the beam has at this point. The beam subsequently passes through a collimating lens 34 and a quarter wave retarder 36, which converts the beam 32 from linear polarization illustrated in the legend 32a to the clockwise circular polarization indicated in the legend 32b.

At this point, the incident compensation beam 32 passes through a reticulated or rectangular diffraction grating 38, which has the effect of splitting the light into a plurality of beams, so that a plurality of focus points as indicated at 32(e) are used by the compensator rather than a single spot. The beam is reflected on the beamsplitter 40, converged by the converging lens 42, and passed through the variable retarder 44, which in the preferred embodiment is a liquid crystal retarder. This retarder changes the polarization of the incident beams from circular polarization to elliptical as illustrated at 32c, still being clockwise in sense.

At this point, the plurality of converging sub-beams of the whole beam 32 from the variable retarder 44 converge, passing through the cornea 10 and lens 14, becoming circularly polarized as indicated at 32d and reflecting as return compensation beam 45 from the posterior surface of the eye lens 14, as illustrated. This reflected or return compensation beam is polarization—shifted by the double-passage through the cornea and lens not only to circular polarization as indicated at 32d, but is shifted to reverse the direction of the circular polarization as a result of the reflection, as indicated at 45a. (For purposes of the claims, the incident and return beams are each treated singularly, but each includes all of the composite beams split out by the diffraction grating and then reconverged.)

The return compensation beam 45 has the polarization states illustrated in the legends 45a–45d, above and to the right of the configuration. Immediately upon reflecting from the lens surface, the right-hand circular polarization is changed to left-hand circular polarization 45a, and shifts to elliptical polarization as indicated at 45b upon passage through the cornea 10 and lens 14. The return compensation beam 45 passes through the variable retarder 44 where its polarization is restored to circular polarization as indicated in 45c, and travels back through the elements that the impinging beam went through, passing through a polarization shift at 45d until the beam arrives at the polarizing beamsplitter 30.

It will be remembered that when the beam initially passed up through this beamsplitter, it was transversely polarized as indicated at 32a. It is a property of a polarizing beamsplitter to transmit light that is polarized perpendicularly to its reflecting surface, and to reflect light that is polarized parallel to its reflecting surface. As the return compensation beam is now completely linearly polarized, parallel to the reflecting surface of the beamsplitter 30, the return compensation beam 45 is reflected to the right, towards the photodetector 46. The return compensation beam is focused by the lens 34 onto the pinhole 47 in front of the photodetector 46. The pinholes 47 and 28 are located in optically conjugate planes to the focal points formed at the posterior surface of the lens. This confocal arrangement causes stray light reflected from other areas than the focal points to be blocked by the pinhole 47 without reaching the photodetector 46.

In other words, when all light of the return beam 45 impinging downward upon the polarizing beamsplitter 30 is linearly polarized orthogonally to the direction of the upwardly travelling beam 32, all of the light reflected from the surface of the lens 14 would travel through to the photodetector 46. Thus, absent the polarization shift effected by the anterior segment of the eye, incident and return compensation beams 32 and 45 would have the polarization states shown at 32a and 45d, respectively. The variable retarder is adjusted to maximize the intensity of light in the polarized state shown at 45d as closely as possible.

The photodetector 46 outputs a voltage signal corresponding to light intensity that feeds back into the circuit 49. Because the cornea and lens shift the polarization, the variable retarder is varied by the circuit 49 until the electric signal coming from the photodetector 46 is maximized. FIG. 2 illustrates states of polarization of incident and return beams after the compensator has already been adjusted to compensate for anterior segment polarization shift. After the variable retarder 44 has been adjusted for the optimal compensation of corneal and lenticular polarization distortion, the ellipsometer 24 is free to pass its incident diagnostic beam 48 through the beam-splitter, having its beam polarization-compensated by the variable retarder (compensator) 44, and receive a return beam 50 that actually reflects not the polarization distortion caused by the cornea and lens, but only that of the nerve fiber layer in question. This polarization information is then captured and can be analyzed according to ellipsometry techniques that are known in the prior art or as set forth in this disclosure.

This process has been disclosed having the incident and return compensation and diagnostic beams double-passing the variable retarder 44. However, only one of the compensation beams and one of the diagnostic beams would have to pass through the variable retarder, either the incident or return beam. The simplest geometry producing the most accurate results involves double-passing both beams as shown.

Figure 4:
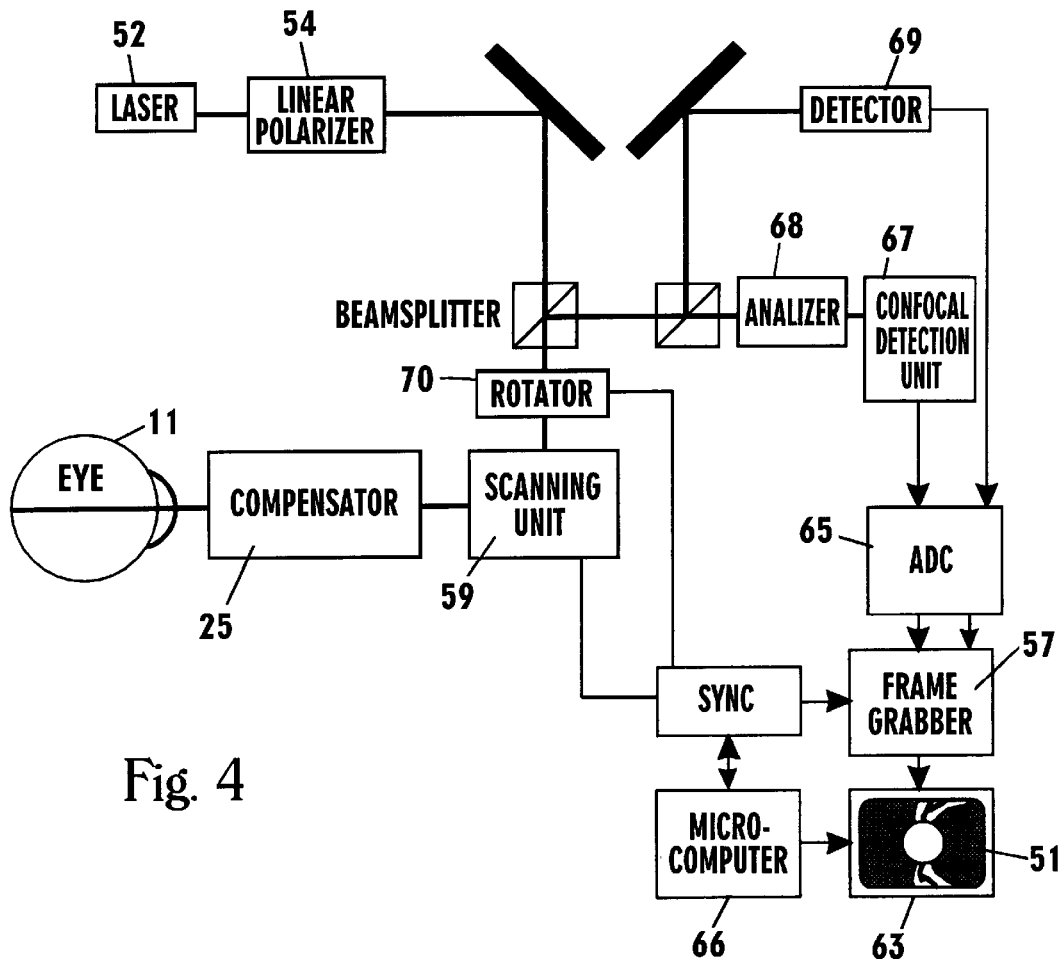
FIG. 4 illustrates a topographical mapping system.
Figure 7:
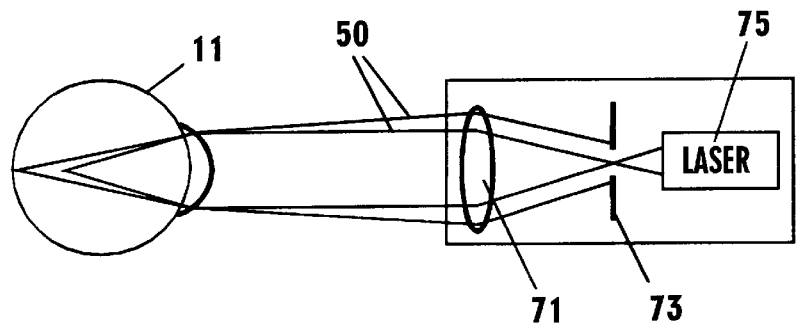
FIG. 7 is a diagrammatic illustration of a photodetector incorporating a focusing lens and a pinhole diaphragm for use in confocal detection techniques.

The corneal polarization compensator 44 is used in all of the techniques that are discussed in this disclosure. It has already been stated that the ellipsometer can be used basically by itself, as shown in FIG. 2, along with scanning and analysis equipment, not shown in FIG. 2, to provide a useable map of the thickness of the retinal nerve fiber layer. A computer frame 51 shown in FIGS. 3 & 4 illustrates the appearance of a typical nerve fiber layer thickness or topographic map.

One way of measuring and mapping the thickness of the nerve fiber layer is shown in FIG. 3, with a system that uses a custom ellipsometer made for this use. It produces an incident diagnostic beam 48 generated by the laser 52, subsequently linearly polarized by linear polarizer 54, converted to circular polarization by quarter-wave retarder 56 and scanned across the ocular fundus by the scanning unit 58. At each point of the scan, the return diagnostic beam 50 is then again scanned by an oscillating mirror 60 sequentially across a plurality of polarizers 62 forming an array. Six polarizers are shown in the array of FIG. 3, and as the return beam reaches the detector 64 in sequence from each of the polarizers the beam intensity is photoelectrically converted by the detector 64 into a signal that is digitized by an ADC (Analog-to-Digital converter) 65 and stored in the memory of the computer 66. From the data stored in the computer, the four elements of the Stokes vector of the incident diagnostic beam 48 are compared to the calculated Stokes vector of the return diagnostic beam, and the change in polarization at the current measuring location is displayed on the CRT display 63. Subsequently, the incident diagnostic beam is guided by the scanning unit 58 to the next measuring site.

The scanned polarizer system of FIG. 3 is diagrammatic, and the polarizers could be either reflective or transparent and would ordinarily have a mirror system converging the respectively produced beams onto the detector. For every point scanned on the ocular fundus, all of the polarizers 62 would be scanned by the oscillating mirror 60.

It would be clear to a person skilled in the art that the principle described can also be performed by changing the time sequence of the polarization data measurement process. For example, instead of scanning a single point at 58 while mirror 60 undergoes a complete scanning cycle, the incident diagnostic beam 48 could first be scanned by the scanning unit 58 over the whole examination area, while the return diagnostic beam 50 is fixed on one of the polarizers, then on to the next. Either way, the data points are aggregated and displayed as an intensity- or color-coded map, for example. Also, illumination of the examination area with a scanning laser could be modified by illuminating the fundus with a static (non-scanning) light source and replacing the detector 64 with a camera.

Thus far, gauging of the thickness of the nerve fiber layer, and the creation of a thickness map display has been discussed. Using a similar technique, a topographic map can be made which is substantially more accurate and detailed than those made with conventional techniques.

FIG. 4 illustrates a system similar to the FIG. 3 setup, which will produce a topographic map of the anterior surface of the retinal nerve fiber layer. The scanning unit 58 is replaced by a three-dimensional scanning unit 59, and the detector 64 is replaced by a confocal detection unit 67. It is similar to the typical confocal system that is now used, except that the optical data that is received back from the nerve fiber layer is sorted by discarding (filtering out) any data, (any light rays) that are returning from the eye having altered polarization. Because the corneal polarization compensator neutralizes polarization shifting caused by the anterior segment of the eye, and the polarization state of the incident light beam is known, any return light which does not match the incident beam in its state of polarization is known to have been reflected from a surface deeper than the nerve fiber layer surface 16. Conventional confocal topographical mapping is enhanced by discarding this light information, which represents false data. Mechanically this is done by scanning across the entire surface of the nerve fiber layer in progressively deeper focal planes and generating an intensity map, and repeating for consecutively deeper layers. The analyzer 68 includes a filter polarized parallel to the incident beam, attenuating light of other polarization states, and the computer stores an intensity map for each plane. These maps are software-overlaid, and the brightest return plane for each point across the fundus is considered to be the depth of the front of the nerve fiber layer at that point. This can actually be done with a single scan by using two confocal detectors focused just to the far and near sides of the anterior surface, respectively, and interpolating from the relative intensities at each point.

The potential information that can be gleaned from the interior of the eye utilizing corneal compensation is considerable. For example, topographic maps of deeper layers of the eye than the surface of the nerve fiber layer can be made by rejecting the light in the polarization state of the initial beam, rather than vice-versa.

Figure 5:
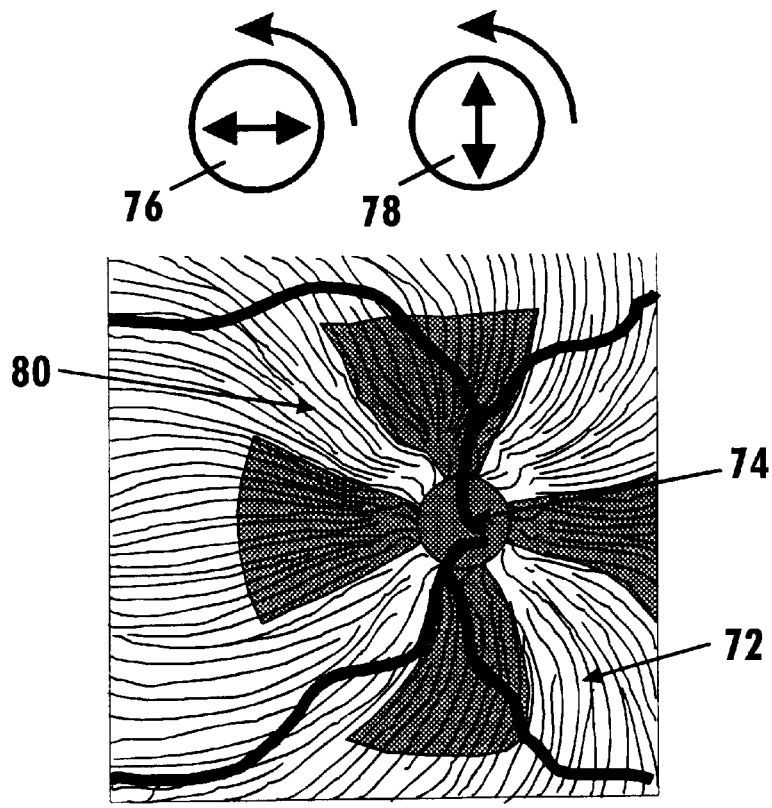
FIG. 5 illustrates the appearance of the retinal nerve fiber layer under illumination with linearly polarized light and detection with a crossed polarizer, corneal birefringence being eliminated.
Figure 6:
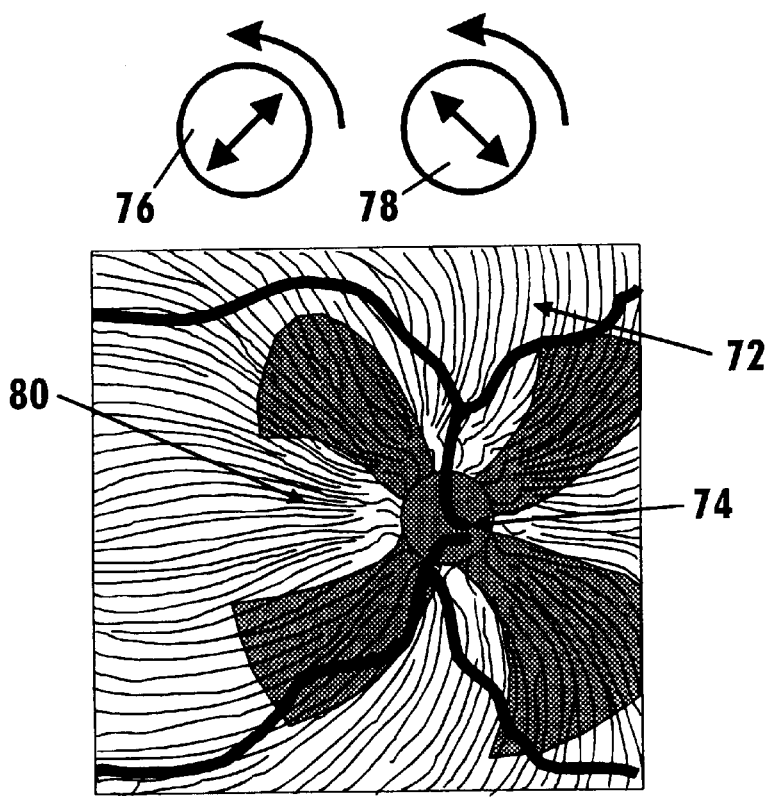
FIG. 6 is identical to FIG. 5, but illustrating measurement taking place with the orientation of the polarization axis of the illuminating beam and detection filter being rotated about 45 degrees.

Returning from tomography to thickness mapping again, the same setup shown in FIG. 4 used for topographic map-making can be used to produce an enhanced nerve fiber thickness map. A polarization rotator 70 is interposed in the light path of the incident or return diagnostic beam, or both. A second detector 69 measures the absolute intensity of the return diagnostic beam independent from its polarization state. Referring to FIGS. 5 & 6, the retinal nerve fiber layer 14 comprises an array of radially arranged nerve fibers 72 which converge to form the optic papilla 74. The fibers are about half the diameter of the wavelength of visible light in width. Because the array exhibits local parallelism and wavelength-order-of-magnitude spacing, it exhibits directional birefringence.

It is illuminated with linearly polarized light, and the reflected light from the fundus is passed through an analyzer with an orthogonally polarized filter 68 to a photodetector or collector. The states of polarization of the incident beam and the filter are diagrammed at 76 and 78. A cross pattern of brightness, indicated at 80, will appear at the detector. There will be darkness along the polarization axes of both the incident light beam and the analyzer filter. The bright arms correspond to areas of the nerve fiber layer having fiber orientation rotated 45 degrees to either side of the polarization axis of the incident beam and the analyzer filter. The bright portions of the cross provide an accurate indication of the thickness of the nerve fiber layer at these points, as substantial change in polarization caused by substantial nerve fiber layer thickness will shift the polarization of the light adequately to pass through the analyzer polarization filter.

In order to obtain a best measurements, the polarization axes of the incident beam and analyzer filter are synchronously rotated through 90 degrees, which constitutes a complete rotation cycle, with a brightness reading taken about every 2 degrees, for every point on the fundus that will appear on the map. The polarization axis can be held at one orientation (actually rotating through 2 degrees) while the entire fundus is scanned and then "incremented" 2 degrees for the next scan until all test orientations of the polarization axis have been sampled for the entire field. Or, in reverse, completing a full polarization axis rotation cycle at each point on the fundus before moving on.

The brightest return beam is thus picked up for every point in the field. These brightest points are cumulated and formed into an intensity map corresponding point-to-point to the relative thickness of the fundus.

The second photodetector 69 is used to measure the total amount of reflected intensity of the return diagnostic beam at the corresponding points on the fundus. By normalizing the intensity values obtained with the first photodetector 67 with the corresponding intensity values obtained with detector 69, absolute changes in the state of polarization of the return diagnostic beam are calculated. This permits variations in return beam intensity caused by factors other than polarization shifting to be factored out of the final data.

A substantially identical technique with different computer handling of data produces a nerve fiber orientation map. The orientation of maximum return beam intensity at each point represents alignment of the beam and filter polarization axes with the optic axis of the nerve fiber layer.

Figure 8:
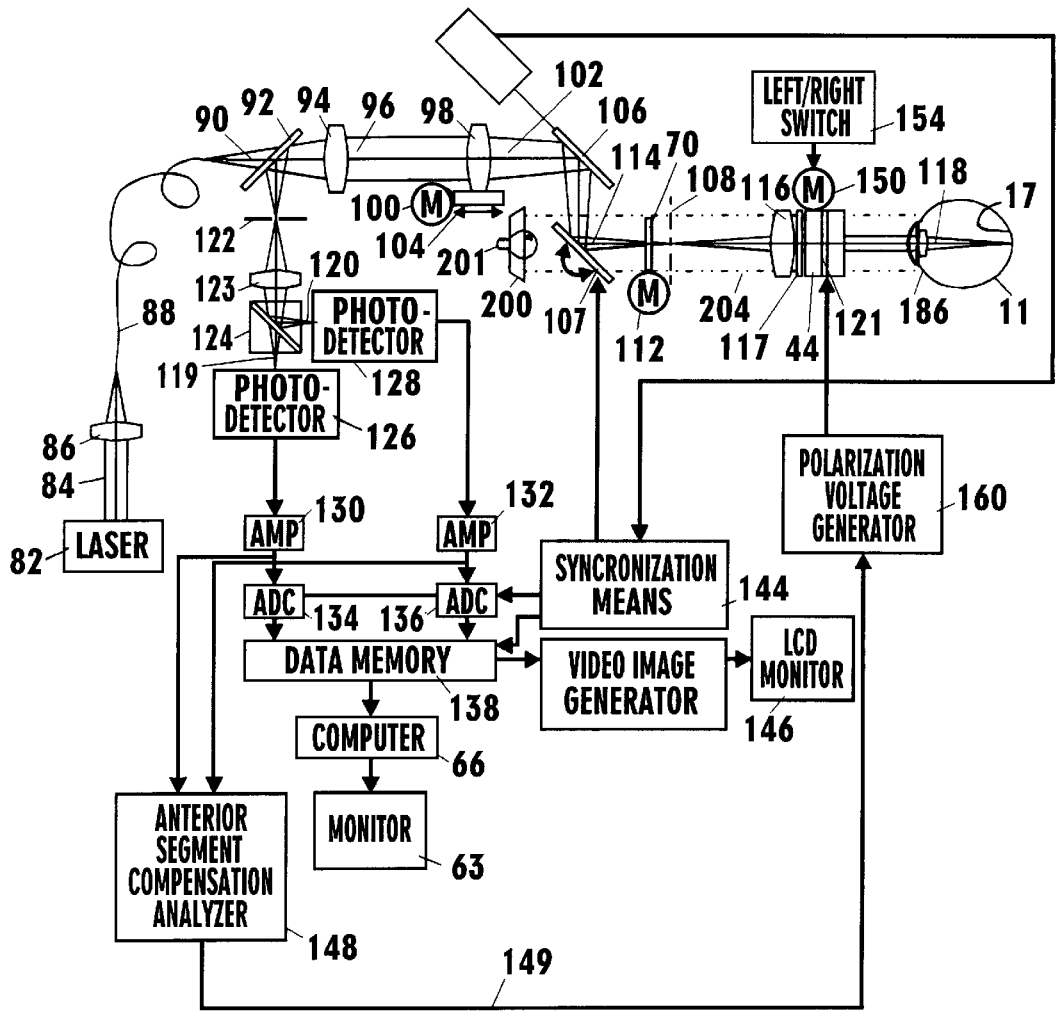
FIG. 8 is a diagrammatic view of one example of the system as currently used.

An example of an implementation of a preferred embodiment of the invention is illustrated in FIG. 8. To avoid confusion between parts in various embodiments having overlapping or different functions, the elements in FIG. 8 are assigned fresh numbers even though they may be substantially parallel to elements previously illustrated.

A polarized diode laser 82 of wavelength 780 nm acts as the light source of the instrument. Although light of any wavelength that passes the ocular media can be employed, a diode laser of wavelength 780 nm is an excellent compromise between optical performance, patient comfort, and laser safety. The linearly polarized laser light 84 is focused by the coupling lens 86 onto a polarization maintaining, single-mode optical fiber 88. The diverging light beam 90 emerging from the optical fiber impinges upon the beam splitter 92.

The beam splitter 92 may be a polarizing beam splitter, a non-polarizing beam splitter or a partially polarizing beam splitter. In the described preferred embodiment, the beam splitter reflects roughly 99% of light polarized perpendicular to the plane of incidence, and it transmits about 85% of light polarized parallel to the plane of incidence. With the diverging light beam 90 emerging from the optical fiber substantially being polarized parallel to the plane of incidence, about 85% of the laser light impinging upon the beam splitter is transmitted and is collected by the lens 94 generating a collimated light beam 96. The collimated light beam 96 is made convergent by the focusing lens 98 which is mounted onto the focus translation stage 104. A stepper motor 100 is used to move lens 98 by computer control.

Consequently, the converging light beam 102 is deflected by the resonant scanner 106 to scan in the horizontal direction at a frequency of about 4500 Hz and the galvanometer scanner 107 in the vertical direction at a frequency of about 30 Hz, generating a focused two-dimensional laser raster 108. At each point of the scan, the scanned laser light penetrates a polarization rotator, consisting of a half-wave plate 70 and the stepper motor controlled drive mechanism 112. The polarization rotator rotates the polarization axis of the scanned converging light beam 114 without (geometrically) rotating the two-dimensional laser raster 108. Alternatively, a liquid crystal device or any other variable retarder can be used as a polarization rotator.

The focused two-dimensional laser raster 108 is imaged by the lens 116 onto the fundus 17 of the eye 11 through the variable retarder 44, the cornea 10, the pupil 13 and the crystalline lens 14. By moving lens 98, the focused raster scan pattern can be imaged onto different layers of the eye fundus 17. The illuminating light beam 118 is specularly reflected from the internal limiting membrane 16 of the eye fundus, generating the specular reflection light beam 119. The state of polarization of the specular reflection light beam 119 is substantially identical to the polarization state of the illuminating light beam 118, except for a 180° phase shift occurring during specular reflection. The remainder of the illuminating light beam 118 penetrates the form-birefringent retinal nerve fiber layer 18 and is partially reflected by retinal layers more posterior than the nerve fiber layer, therefore effectively double-passing the retinal nerve fiber layer 18 and forming the diffuse reflection light beam 120. Because of the form-birefringent properties of the retinal nerve fiber layer, the state of polarization of the diffuse reflection light beam 120 is changed compared to the state of polarization of the illuminating light beam 118.

The specular reflection light beam 119 and the diffuse reflection light beam 120 exit the eye 11 through the crystalline lens 14, the pupil 13 of the iris 12, and cornea 10, and travel back along substantially the same optical path as described above until they impinge upon the beam splitter 92 where they are separated from the diverging light beam 90. Lens 94 focuses the specular reflection light beam 119 and the diffuse reflection light beam 120 onto the pinhole aperture 122 which is located at a plane conjugate to the exit aperture of the optical fiber 88, the plane of the focused two-dimensional laser raster 108, and to the eye fundus 17.

The specular reflection light beam 119 and the diffuse reflection light beam 120 passing through the pinhole are separated by the polarizing beam splitter 124 or a similar arrangement of polarizers and beam splitter. The polarizing beam splitter transmits all light that has a state of polarization identical to the state of polarization of the diverging light beam 90 allowing it to be imaged onto photodetector 126. Any light component that deviates in its state of polarization from the state of polarization of the diverging light beam 90 is reflected by the beam splitter 124 and imaged onto photodetector 128. The output signals of the photodetectors 126 and 128 are amplified by the amplifiers 130 and 132 and digitized by the analog-to-digital converters 134 and 136. The amplified and digitized outputs of the photodetectors are then stored in a dual ported data memory 138 which is accessible by the computer 66 and the video image generator 142.

A synchronization means 144 is triggered by the oscillating frequency of the resonant scanner 106 and generates the driving signal for the galvanometer scanner 107. In addition, the synchronization means 144 controls the memory location address within the data memory 138 so that each amplified and digitized output of each of the photodetectors can be correlated with the scan position of the resonant scanner 106 and galvanometer scanner 107 at the time of data sampling. Typically, 256 data samples of each of the photodetectors are acquired, digitized, and stored along one horizontal scan line, and 256 scan lines at gradually changing vertical positions are acquired before the scan procedure is repeated.

The video image generator 142 immediately reads the data samples from the dual ported data memory 138 and generates a video image that is displayed on a liquid crystal display device 146.

In parallel to the data acquisition process described above, the amplified output signals of the photodetectors 126 and 128 are analyzed by the anterior segment compensation analyzer 148.

Assuming that there would be no polarization effect of the anterior segment of the eye, then a specular reflection light beam 119 would substantially show the same state of polarization as the diverging light beam 90, and, therefore would be completely imaged onto photodetector 126. Light imaged onto photodetector 128 would consist only of the diffuse reflection light beam 120. However, as the anterior segment of the eye is polarizing, the state of polarization of the specular reflection light beam 119 is changed, i.e. there will be an additional component of light detected by photodetector 128, and the output signal of photodetector 126 will be reduced.

The variable retarder 44 is a combination of a plurality of fixed optical retarders, including a layer of liquid crystal material 121. The variable retarder 44 can be rotated along its axis via a motor 150 and a drive belt 152. A proximity switch 154 located in the tabletop 156 automatically detects the position of the eye disease examination device 174 in order to determine if the left or right eye is being examined. The left/right eye signal of the proximity switch 154 is used to control the motor 150 which rotates the variable retarder 44 so that the optic axis of the variable retarder substantially coincides with the optic axis of the cornea 10 of the human eye, which is about 15° nasally downward.

A varying voltage signal generated by the polarization voltage generator 160 and applied to the variable retarder 44 varies the polarization properties of the liquid crystal layer 121 and, therefore, the amount of change in the state of polarization introduced to a light beam passing through the variable retarder. Other fixed or variable retarders or combinations thereof, i.e. Pockets cell, Kerr cell, Soleil-Babinet retarders, combinations of rotating fixed retarders, etc., could be employed instead of the liquid crystal cell described in this preferred embodiment.

A closed loop circuit 149 changes the output of the polarization voltage generator 160 until the signal output of photodetector 126 is maximized and the signal output of photodetector 128 is minimized. At this status, the amount of change in the state of polarization introduced to a light beam passing through the anterior polarization compensator effectively cancels the amount of change in the state of polarization introduced to the same light beam passing through the anterior segment of the eye.

Once the anterior segment polarization effects are cancelled, the signal outputs of photodetectors 126 and 128 can be used to analyze the topography and the thickness of the retinal nerve fiber layer.

Compensation is done automatically with real-time feedback, but is required only once at the beginning of a scanning session rather than having to be updated for every scanned point. Although anterior segment retardation varies somewhat from point-to-point across the cornea, only one point is penetrated by the diagnostic beam in a scanning session.

In another example of an apparatus that can generate a continuously updated thickness map of the retinal nerve fiber layer, the polarization rotator 70 is removed and the variable retarder 44 is automatically adjusted so that the retardation introduced by the variable retarder and the anterior segment is 90°. Then, the combination of variable retarder 44 and anterior segment would represent a quarter-wave retarder transforming the linearly polarized light of the converging beam 114 into circularly polarized light. (This can also be accomplished by inserting a quarter-wave plate 117 into the optical pathway and compensating the anterior segment as described before.)

Light reflected from the eye fundus 17 without a change in its state of polarization passes through the combination of the anterior segment and variable retarder 44 and is transformed back into linearly polarized light with its polarization axis rotated by 90° with respect to the polarizing axis of the diverging light beam 90. This light will be detected by photodetector 128. Any light that was changed in its state of polarization due to the retinal nerve fiber layer will be detected by photodetector 126. Using electronic circuitry 148 performing basic mathematical transformations between the data signals from the photodetectors 126 and 128, a real time thickness map of the retinal nerve fiber layer under examination can be produced and displayed on the LCD monitor 146.

Figure 9:
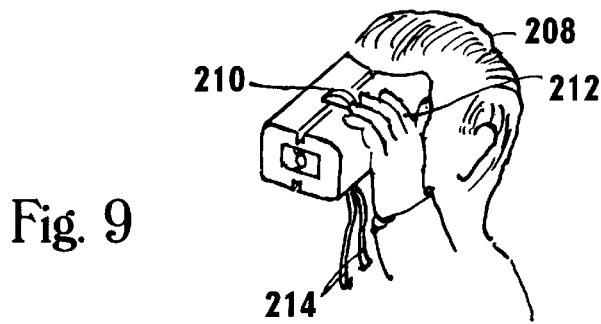
FIG. 9 is an illustration of a hand-held portable modification.

In the drawings, beginning with FIG. 9, the physical manifestation of the retinal eye disease diagnostic system 174 in accordance with the principle of the present invention is displayed. The eye disease diagnostic system is contained in a housing 175 that encloses the optical components, the laser 82, the focusing mechanism 104, the electronic circuit boards and the liquid crystal display monitor 146. The housing 175 is mounted on a cross-slide base 190 and sits on top of the tabletop 156 that, in turn is supported by a commercially available instrument stand. The tabletop 156 also supports the chin rest 172 with fixation light 194 and the power supply 192.

The layout of the patient, the operator, and the apparatus in a typical examination situation is diagrammatically illustrated in FIG. 13. The patient uses seat 170 and rests his/her chin on the chin rest 172 of the apparatus 174, as can best be visualized in FIG. 10. The patient is asked to look at the external fixation light 194 or, alternatively at an internal fixation light within the apparatus 174. A ring projector 200 is illuminated by a light bulb 201 and projects an annular light beam 204 which is imaged by lens 116 onto the front of the patient's eye 11 creating a centering light ring 186 coaxial with the (invisible) laser beam 118. The operator can move the apparatus 174 sideways, forward, and backwards by tilting the joystick control 178 to the desired direction. By rotating the joystick control 178, the apparatus can be raised or lowered with respect to the patient's eye. The operator adjusts the apparatus using the joystick control 178 until the centering light ring 186 is centered around the patient's pupil and is focused onto the patient's cornea 10. Because it is a ring, it encircles but does not touch the pupil 13 and is not seen by the patient. It does not cause the pupil to contract, as otherwise visibility and beam access to the eye would be compromised.

As soon as the centering light ring 186 is centered around the pupil 13, the laser beam 118 of the apparatus can enter the eye, and light reflected from the eye fundus 17 is detected as described above. The light detected is displayed on the LCD 146 which is implemented in the front of the apparatus 174, therefore allowing the operator to observe the live retinal image on the LCD 146 and the patient's eye substantially simultaneously, without having to look to the side of the CRT monitor 63 which would be distracting to the eye examination procedure. The CRT display may be coupled to the operation of the apparatus in real time, or with a slight delay.

Observing the image of the eye fundus on the LCD monitor 146, the operator can focus the image with the focus control 196 which moves lens 98 along its axis. The field of view can be changed by selecting the desired field of view with the field of view selector switch 199. Changing the setting of this switch substantially changes the amplitude of oscillation of the resonant scanner 106 and galvanometer scanner 107.

The operator can adjust the area of the eye fundus to be examined horizontally by swinging apparatus 174 to the left or the right, and vertically by turning the vertical adjustment knob 198 which electronically controls a bias voltage applied to the galvanometer scanner 107 causing the focused laser scan raster 108 to be moved vertically.

It should be clear to a person trained in the art that the functions of horizontal and vertical alignment could also be achieved by mechanical means like tilting the apparatus 174. With the use of appropriate adapters, the apparatus could also be mounted to existing ophthalmic equipment like slitlamp biomicroscopes or fundus cameras.

Figure 18:
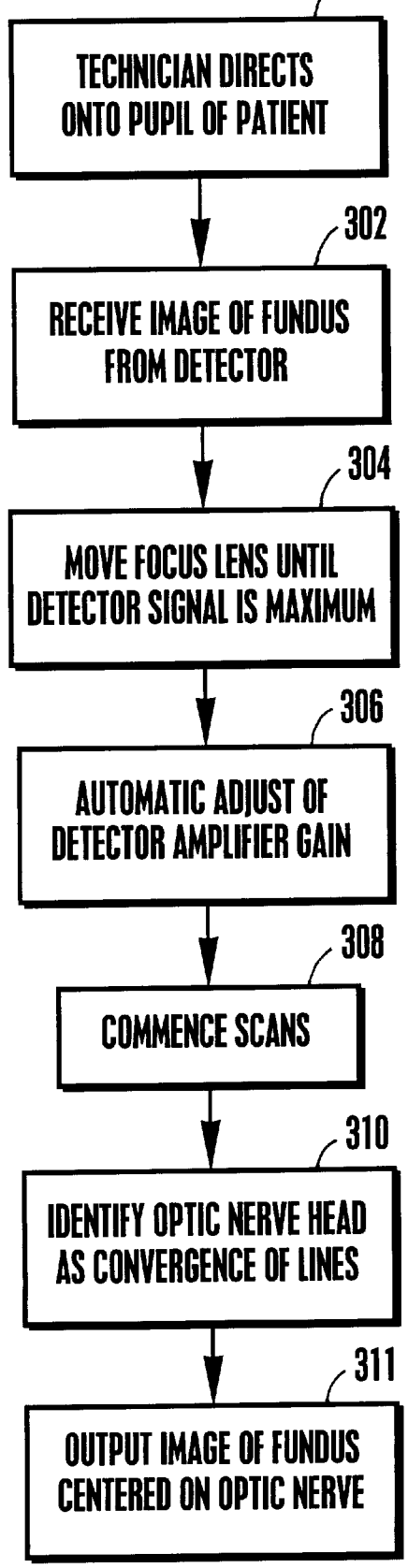
FIG. 18 is a flow chart showing the logic for automatically directing the beam onto the center of the fundus in response to a technician directing a guide beam onto the pupil of a patient.

It should also be clear that, for the functions described in this disclosure, the apparatus 174 could be a hand-held apparatus without the need for a cross-slide base 190 or chin rest 172. Such an apparatus is shown in FIG. 18, wherein the entire unit is about the size of large binoculars and is held and stabilized by the patient. All beam generating, scanning and detecting functions take place inside the compact housing 206 which is held by the doctor 208. Focus knob 210 and a starter switch button 212, obscured in FIG. 18 by the doctor's hand, are all the controls needed since the other adjustments of the console model can be made by body movement. The information signal outputs to a processor through a cable 214, alternative to having on-board non-volatile storage media and drive.

In summary, using the illustrated systems and described methods, three basic types of measurements are possible, producing three different maps. These are, (1) nerve fiber layer surface topography, (2) nerve fiber layer thickness, and (3) nerve fiber orientation.

The first measurement produces improved results over existing techniques, whereas the second and third techniques, thickness and fiber orientation mapping, represent new tools in eye disease diagnosis and, in many cases, provide clinically significant and useful data for the first time.

Two detector systems are shown, the ellipsometer of FIG. 2 and the 6-polarizer array of FIG. 3 (actually just another way to make an ellipsometer). Either could be used in any of the described techniques, and many other configurations can be arranged.

Any of the setups can be modified for confocal detection or not, confocal detection only being necessary in tomographic mapping. Modulation of one or both of the incident and return modulation beams, by rotation of the polarization axis produces more accurate and highly resolved thickness maps, and is necessary in fiber orientation mapping, but is less useful in tomography as light altered at all in its polarization state is discarded.

The feasibility of all of the disclosed diagnostic techniques and equipment depends on the polarization characteristics of the ocular fundus, and further depend on the compensating capability of the corneal polarization compensator to produce the most useable results. These polarization-based diagnostic techniques contribute substantially to repertory of tools and techniques used to accurately diagnose diseases of the eye, and especially for the early diagnosis of glaucoma.

The first technique results in topographic images which are greatly enhanced in resolution and accuracy compared to topographic maps produced by currently used methods. The second and third procedures, nerve fiber layer thickness mapping and fiber orientation map production, go beyond improvements to existing techniques and represent new tools in eye disease diagnosis. The results of these tests provide information previously unavailable to the medical profession. For the first time, detailed, high-resolution, accurate displays of the nerve fiber layer thickness, the wellspring of glaucoma diagnosis source data, and a map tracing the actual physical connection between specific nerves and blind spots in the field of vision characteristic of optic nerve deterioration, are available to the diagnostician.

In addition, polarization information could be used directly for diagnosing diseases by probing other parts of the eye. The discussion thus far has centered around cancelling the polarization effect of the anterior segment, but this could be reversed. For example, the voltage required to null the effect of the anterior segment correlates with corneal polarization shifting, so the voltage generated by the polarization voltage generator 160 to compensate for the cornea polarization could be sampled, transformed into the respective retardation value of the anterior segment and used to calculate the thickness, density or stress of the cornea and/or the lens.

Although the apparatus is disclosed for use in diagnosing eye disease, it could be adapted for use in any situation presenting similar challenges, i.e. where an accurate depth or thickness measurement or tomographic mapping is required, but the object or region being mapped is sub-surface and is itself birefringent, or borders on a birefringent medium. For example, other parts of the body than the eye could be subjected to the same technique.

There may be industrial uses as well, although the in vivo requirement defines much of the challenge met by the invention, since the object of investigation cannot be dismantled. In situations in which post-manufactured measurements are required for quality control, for example, the technique might have application. The thicknesses of layers of an integrated circuit could be ascertained. A test workplace with semi-transparent layers and one or more birefringent layers could be laid up to establish the viability of a production technique. In situations in which X-ray examination, magnetic resonance imaging, and other sub-surface probing techniques might not work, polarization-principle probes of the general nature of those described might be useful.

FIG. 18 shows the logic for automatically directing and focussing the diagnostic beam onto the optic nerve in the fundus in response to a technician simply directing a visible guide beam onto the patient's pupil. Thus, the present logic avoids the need for a technician to know what a fundus looks like to direct an invisible diagnostic beam thereon; instead, the technician need only direct a visible guide beam (that is generally colinear with the diagnostic beam) onto a portion of the eye (the pupil) that is easily recognizable to the technician's naked eye.

The flow charts herein illustrate the structure of the logic of the present invention as embodied in computer program software. Those skilled in the art will appreciate that the flow charts illustrate the structures of logic elements, such as computer program code elements or electronic logic circuits, that function according to this invention. Manifestly, the invention is practiced in its essential embodiment by a machine component that renders the logic elements in a form that instructs a digital processing apparatus (that is, a computer) to perform a sequence of function steps corresponding to those shown.

In other words, at least portions of the flow chart shown in FIG. 18 may represent a computer program that is executed by a processor within a computer as a series of computer-executable instructions. These instructions may reside, for example, in RAM of the computer 66, or the instructions may be stored on a DASD array, magnetic tape, hard disk drive, electronic read-only memory, or other appropriate data storage device. In an illustrative embodiment of the invention, the computer-executable instructions may be lines of compiled $C^{++}$ compatible code, or any other machine code.

Commencing at block 300, a technician directs a guide beam onto the visibly central portion, i.e., the pupil 13, of the eye of the patient by, e.g., moving the joystick 178 mentioned above. The guide beam consists of one or more pinpoint beams or an annular beam that surrounds the pupil, and it is colinear with the invisible diagnostic beam of the optics system disclosed above. As the guide beam is directed onto the pupil, the diagnostic beam is directed along the guide beam into the eye. In accordance with prior disclosure, the diagnostic beam is reflected from the eye fundus 17, and the reflected beam is detected by a detector which generates an image signal in response thereto, with the image signal being sent to a computer, e.g., the computer 66, for analysis.

The image of the fundus is received at block 302. Moving to block 304, the present invention focusses the diagnostic beam onto the optic. This focussing can be done manually by turning the focus control 196 (FIG. 10) to move a focussing lens, e.g., the lens 98 (FIGS. 8 and 12) to thereby focus the diagnostic beam onto the optic nerve. Proper focus is indicated when the intensity of the signal from the detector is maximized. For instance, when the detector incorporates an amplifier having automatic gain control (AGC), the AGC seeks to minimize the amplifier gain at block 306 and thereby focus the system.

Or, the above-mentioned focussing steps can be undertaken automatically. More particularly, at block 304 the computer 66 can generate a focus signal to cause, e.g., the focus control 196 (FIG. 10) to move a focussing lens, e.g., the lens 98 (FIGS. 8 and 12) to thereby focus the diagnostic beam onto the optic nerve. In undertaking the focussing step, the logic varies the focus until the intensity of the signal from the detector is maximized, or until the gain of the detector amplifier is minimized under AGC control. As still another alternative, focus can be indicated when width of the nerve fiber lines in the image from the detector is minimized.

Then, at block 308 diagnostic scans are undertaken as discussed previously. These scans encompass a relatively large angle, e.g., about forty degrees (40°). With this wide scan angle, when the guide beam is directed at the pupil, the diagnostic beam will be directed sufficiently close to, if not on, the optic nerve location, i.e., the center of the fundus.

As recognized by the present invention and shown in FIGS. 5 and 6, the fundus includes nerve fibers 74 that converge to establish the optic nerve (papilla) 74. With this in mind, at block 310 in FIG. 18 the present logic receives the image signal and identifies the center of the fundus (generally, the optic nerve) as being the convergence point of the nerve fiber lines in the image signal.

Having identified the optic nerve, the logic moves to block 311 to output an image of the fundus centered on the optic nerve. The output image encompasses an angle, from end to end, that is less than the angle covered by the scan. Thus, even when the diagnostic beam is not centered on the optic nerve, it will be sufficiently close to it, when the guide beam is directed on the pupil, to enable the generation of an image centered on the optic nerve.

Alternatively, if desired, the computer can generate a steering signal that is used by, e.g., a stepper motor that is coupled to the joystick 178 (FIGS. 10 and 11) to move the joystick 178 and thereby move the diagnostic beam directly onto the optic nerve 74, if the diagnostic beam is not already directed precisely thereon. Thus, the skilled artisan can now appreciate that the diagnostic beam initially is directed somewhere near the optic nerve when the technician directs the guide beam onto the pupil, with final steering of the diagnostic beam directly onto the optic nerve being undertaken by the computer 66, if desired.

While the above disclosure contemplates analysis of the data by a computer 66 that is local to the optics system, the present invention envisions a system wherein an optics and detection system as disclosed above generate a signal that is transmitted off-site to a remote computer for analysis. By "remote" is meant off-site, i.e., not located in the same facility as the optics and detection systems.

Figure 19:
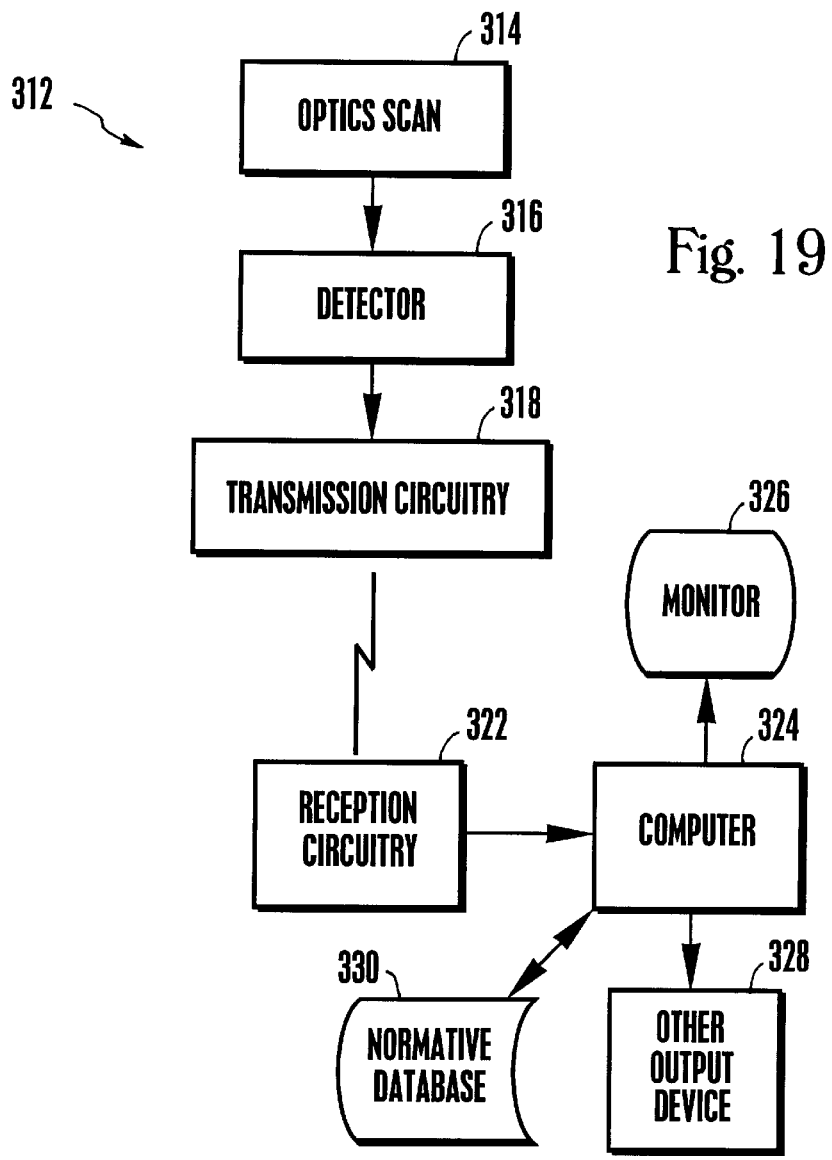
FIG. 19 is a block diagram of a system wherein data is collected by an optics system and then transmitted off-site for analysis at a remote data analysis facility.

FIG. 19 shows such a system, generally designated 312. An optics system 314 with detector 316 are in all essential respects identical in configuration and operation to the above-described optics systems with detector. As shown in FIG. 19, however, the signal from the detector 316 is sent to a transmission circuit 318 for transmission of the signal via a communication link 320 to a remote reception circuit 322. The link 322 can be a radiofrequency (rf) link, in which case the transmission circuit 318 and reception circuit 322 are conventional radio transceivers. Or, the link 322 can be telephone wire, optical fibers, or coaxial cable, in which case the transmission circuit 318 and reception circuit 322 include modems and other conventional transmission and reception circuitry known in the art.

The received signal is sent from the reception circuit 322 to a computer 324 that is remote from the optics system 314, i.e., that is in a facility that is distanced from the optics system 314. The computer 324 analyzes the image data and outputs the analysis on a video monitor 326 or other output device 328.

In analyzing the image data the computer 324 accesses a normative database 330. The normative database 330 contains data that is useful for comparing the image data from a patient to a set of data derived from a population of "normal" people of the patient's age, gender, and/or race. As recognized by the present invention, what constitutes a "normal" retinal image depends on one or more of the above factors, particularly age and race. Accordingly, the computer 324 compares the received image data against the appropriate race-normalized data from the database 330 to output a signal representative of whether the image data being analyzed is "normal".

Figure 20:
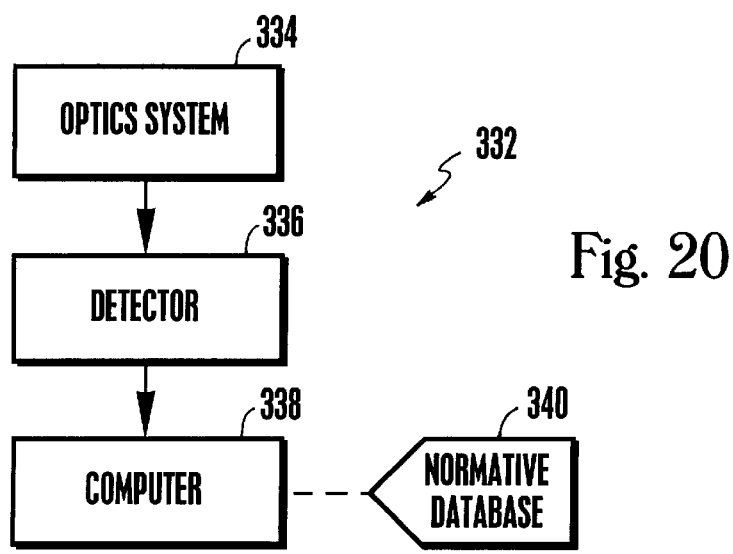
FIG. 20 is a block diagram of a system wherein data is collected by an optics system and analyzed using an on-site computer having access to a normative database.

As an alternative to the remote computer system 312 shown in FIG. 19, FIG. 20 shows a system, generally designated 332, in which an optics system 334 and associated detector 336 generate image signals for analysis thereof by a local computer 338. The user of the system 332 must purchase or license a normative database that is contained on a computer data storage medium 340, e.g., a so-called "smart card" that is accessible to the computer 338, to facilitate normalization of the image data.

While the particular EYE EXAMINATION APPARATUS EMPLOYING POLARIZED LIGHT PROBE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more".

What is claimed is:

1. An apparatus for analyzing an eye having an anterior portion and a posterior portion, comprising:

(a) a polarized light source for producing an incident diagnostic beam of known state of polarization;

(b) an optics system transmitting said incident diagnostic beam into an eye through the pupil, where it is reflected from the interior of the eye as a return diagnostic beam, the optics system collecting said return diagnostic beam and directing same to a polarization sensitive detection device;

(c) a polarization sensitive detection device for collecting and transducing information about the state of polarization of said return diagnostic beam into an electrical signal, the electrical signal being representative of the state of polarization of the return diagnostic beam whereby the electrical signal can be used to indicate the state of polarization of the return beam; and (d) a transmitting circuit receiving the electrical signal and transmitting the signal to a computer, and (e) a computer electrically connected to the detection device and including logic means for directing the diagnostic beam onto an eye of a patient, the logic means including:

means for receiving an image signal representative of an image of a fundus of the patient, the signal being derived from the diagnostic beam, the fundus including an optic nerve location; and means for identifying the optic nerve location.

2. The apparatus of claim 1, further comprising a corneal polarization compensator positioned and configured for modifying the polarization of at least one of said diagnostic beams to thereby facilitate assessment of any alteration of the polarization state of said return diagnostic beam caused by the polarization properties of the posterior portion of the eye.

3. The apparatus of claim 1, wherein the optics system includes at least one focussing lens and the logic means further comprise means for generating a focus signal for use thereof in moving the focussing lens to focus the diagnostic beam onto the optic nerve location.

4. The apparatus of claim 3, wherein the fundus includes nerve fibers defining respective widths, and the means for generating a focus signal causes the focussing lens to move such that the widths are minimized in the image signal.

5. The apparatus of claim 1, wherein the computer is remote from the optics system, and the computer accesses a normative database to compare the electrical signal to at least some elements in the database and to generate an analysis signal in response thereto.

6. The apparatus of claim 1, wherein the computer is local to the optics system, and the computer accesses a removable computer memory device containing a normative database to compare the electrical signal to at least some elements in the database and to generate an analysis signal in response thereto.

7. The apparatus of claim 1, wherein the computer generates a steering signal for use thereof in directing the diagnostic beam onto the optic nerve location.

8. An apparatus for analyzing an eye having an anterior portion and a posterior portion, comprising:

(a) a polarized light source for producing an incident diagnostic beam of known state of polarization;

(b) an optics system transmitting said incident diagnostic beam into an eye through the pupil, where it is reflected from the interior of the eye as a return diagnostic beam, the optics system collecting said return diagnostic beam and directing same to a polarization sensitive detection device;

(c) a polarization sensitive detection device for collecting and transducing information about the state of polarization of said return diagnostic beam into an electrical signal, the electrical signal being representative of the state of polarization of the return diagnostic beam whereby the electrical signal can be used to indicate the state of polarization of the return beam; and (d) a computer electrically connected to the detection device and executing a program of instructions to receive an image signal representative of a fundus and derived from the diagnostic beam, the fundus including an optic nerve location, the computer outputting a signal representing the optic nerve location.

9. The apparatus of claim 8, wherein the optics system includes at least one focussing lens and the computer generates a focus signal for use thereof in moving the focussing lens to focus the diagnostic beam onto the optic nerve location.

10. The apparatus of claim 9, wherein the fundus includes nerve fibers defining respective widths, and the computer causes the focussing lens to move such that the widths are minimized in the image signal.

11. The apparatus of claim 8, wherein the computer is remote from the optics system, and the computer accesses a normative database to compare the electrical signal to at least some elements in the database and to generate an analysis signal in response thereto.

12. The apparatus of claim 8, wherein the computer is local to the optics system, and the computer accesses a removable computer memory device containing a normative database to compare the electrical signal to at least some elements in the database and to generate an analysis signal in response thereto.

* * * * *